(12) United States Patent
Gifford, III et al.

(10) Patent No.: US 6,494,884 B2
(45) Date of Patent: Dec. 17, 2002

(54) METHODS AND DEVICES FOR DELIVERING OCCLUSION ELEMENTS

(75) Inventors: Hanson S. Gifford, III, Woodside, CA (US); Ivan Sepetka, Los Altos, CA (US); Son Gia, San Jose, CA (US); Maria Aboytes, Palo Alto, CA (US)

(73) Assignee: Concentric Medical, Inc., Mountain View, CA (US)

( * ) Notice: Subject to any disclaimer, the term of this patent is extended or adjusted under 35 U.S.C. 154(b) by 50 days.

(21) Appl. No.: 09/780,587

(22) Filed: Feb. 9, 2001

(65) Prior Publication Data

US 2002/0111646 A1 Aug. 15, 2002

(51) Int. Cl.7 .............................................. A61B 17/00
(52) U.S. Cl. ....................................... 606/108; 606/151
(58) Field of Search ................................ 606/151, 108, 606/157, 1, 114, 127, 113, 200

(56) References Cited

U.S. PATENT DOCUMENTS

| | | | | |
|---|---|---|---|---|
| 5,522,836 A | * | 6/1996 | Palermo | 606/108 |
| 5,947,962 A | * | 9/1999 | Guglielmi et al. | 606/108 |
| 5,984,929 A | * | 11/1999 | Bashiri et al. | 606/108 |

* cited by examiner

*Primary Examiner*—Kevin T. Truong
(74) *Attorney, Agent, or Firm*—Hoekendijk & Lynch, LLP (57) ABSTRACT

A device for delivering an occlusion element, or other medical device, which includes a fluid dissolvable bond. The occlusion element is coupled to the delivery element with the fluid dissolvable bond. The bond may be dissolved by delivering a fluid through the delivery element either through the delivery element itself or through a tube positioned in the delivery element.

28 Claims, 12 Drawing Sheets

METHODS AND DEVICES FOR DELIVERING OCCLUSION ELEMENTS

BACKGROUND OF THE INVENTION

The present invention relates to the delivery of medical devices and, in particular, occlusion elements. Occlusion elements, such as coils, are delivered to occlude vascular regions and malformations for various reasons. For example, occlusion elements, such as coils, may be delivered into an aneurysm to occlude the aneurysm. Other uses of occlusion elements include treatment of AVM's and other malformations.

SUMMARY OF THE INVENTION

The occlusion element is coupled to a delivery element with a material which is dissolvable with a fluid. The material forms a dissolvable connection between the delivery element and the occlusion element. The occlusion element is advanced through the patient's vascular system and, at the appropriate time, the material is dissolved. The dissolvable material is preferably dissolved with a fluid which is delivered to the material through the delivery element or through a tube positioned in the delivery element. The fluid may be delivered, withdrawn or otherwise circulated around the material with the tube and delivery element in any suitable manner. Alternatively, the material may be dissolved with the patient's own blood. Finally, the fluid may also be contained within the delivery element but separated from the material until the desired time.

The occlusion element may be embedded in the material. For example, the occlusion element may have a coil, a plurality of filaments, a ball or a cage embedded in the material. The embedded portion may also be in an expanded position when embedded in the material and in a collapsed position after the material is dissolved. For example, the embedded portion may be a stacked coil when collapsed and a stretched coil when embedded in the material. The delivery element may also have a portion embedded in the material such as a number of filaments.

A blocking element may also be provided which protects part of the dissolvable material from exposure to blood or other fluids. The blocking element may be positioned within a cavity in the material. The cavity may be a throughhole through which the fluid is delivered when dissolving the material. The blocking element may also help to protect the connection from kinking and other mechanical disturbances which occur when advancing the occlusion element through small, tortuous vessels. The blocking element can prevent inadvertent mechanical detachment when the device is bent or otherwise deformed during advancement through the patient.

A flexible sheath may also be positioned over the material to protect the material. The sheath may be solid or may have openings or slits therein to promote flow through the sheath when dissolving the material. The delivery element may also have a fluid distributing portion which distributes the fluid for dissolution of the material.

The occlusion element itself may also have a blocking portion which prevents contact between the patient's blood and the material thereby inhibiting premature dissolution of the material. The blocking portion may be a plug of material such as solder.

These and other advantages of the invention will become apparent from the following description of the preferred embodiments, claims and drawings.

DESCRIPTION OF THE PREFERRED EMBODIMENTS

Referring to FIGS. 1–4, a system 2 for delivering a medical device 4, such as an occlusion element 6, is shown. The invention is described in connection with delivery of the occlusion element 6, however, the devices and methods of the present invention may be used to deliver any other medical device without departing from the scope of the invention. The system 2 includes a delivery element 8 to which the occlusion element 6 is mounted. A fluid dissolvable material 10 forms a dissolvable connection between the occlusion element 6 and the delivery element 8. The material 10 is preferably manitol but may be any other suitable material including any sugar, salt or combination thereof.

The occlusion element 6 is shown as a short section of coil for clarity but may be any suitable occlusion element 6 such as those described in U.S. Pat. Nos. 5,855,578, 5,853,418, 5,749,894 and 5,749,891 which are hereby incorporated by reference. In the preferred embodiment, the occlusion element 6 is made of platinum wire or ribbon which forms coils 7. Of course, any suitable materials and structure may be used to form the occlusion element 6. The delivery element 8 is preferably a tube 11 having at least one lumen 12, however, the delivery element 8 may also be a solid element such as a wire or mandrel without departing from the scope of the invention. The occlusion element 6 is mounted to the end of the delivery element 8 and extends from the delivery element.

Figure 1:
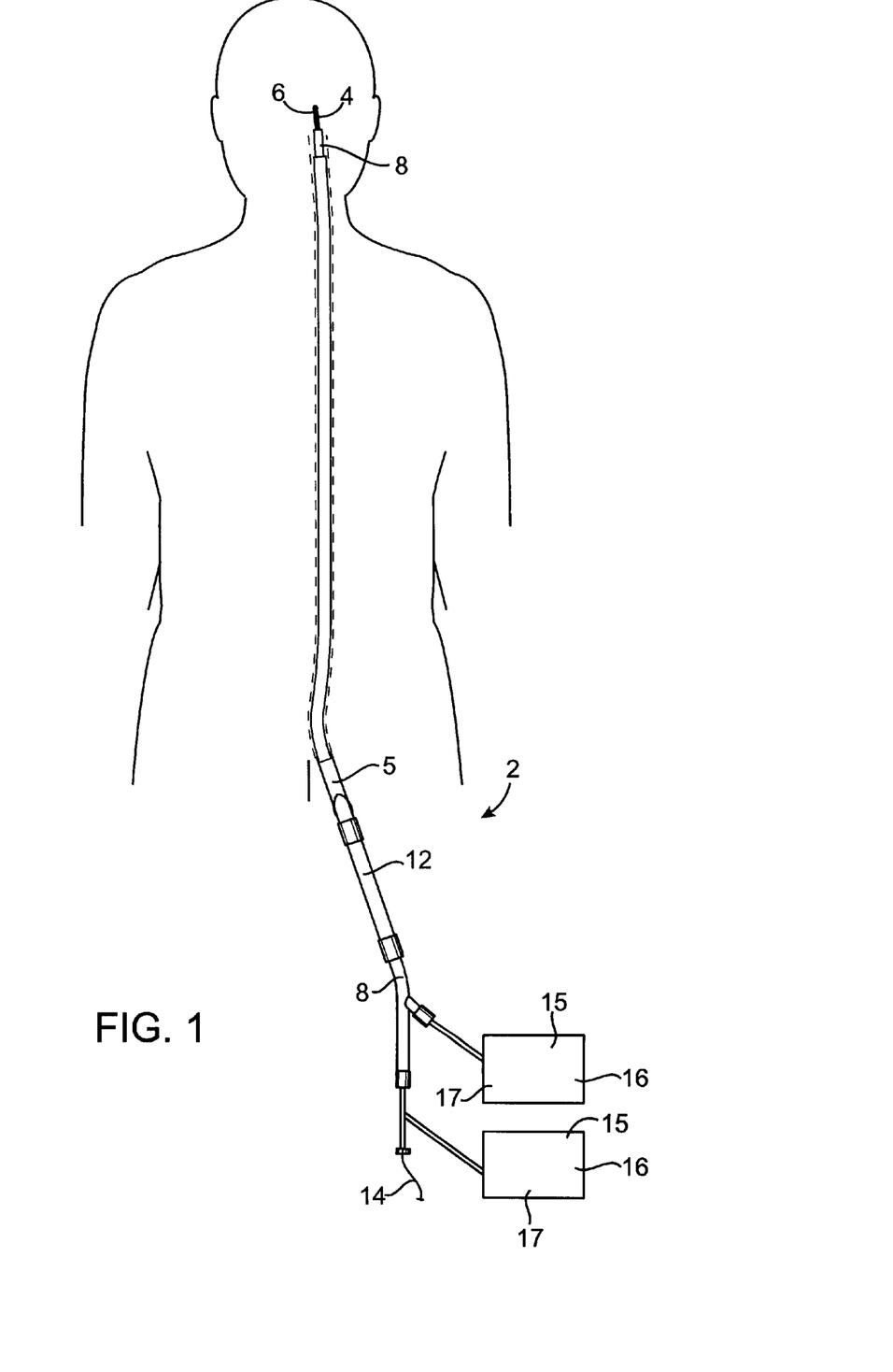
FIG. 1 shows a system of the present invention.
Figure 2:
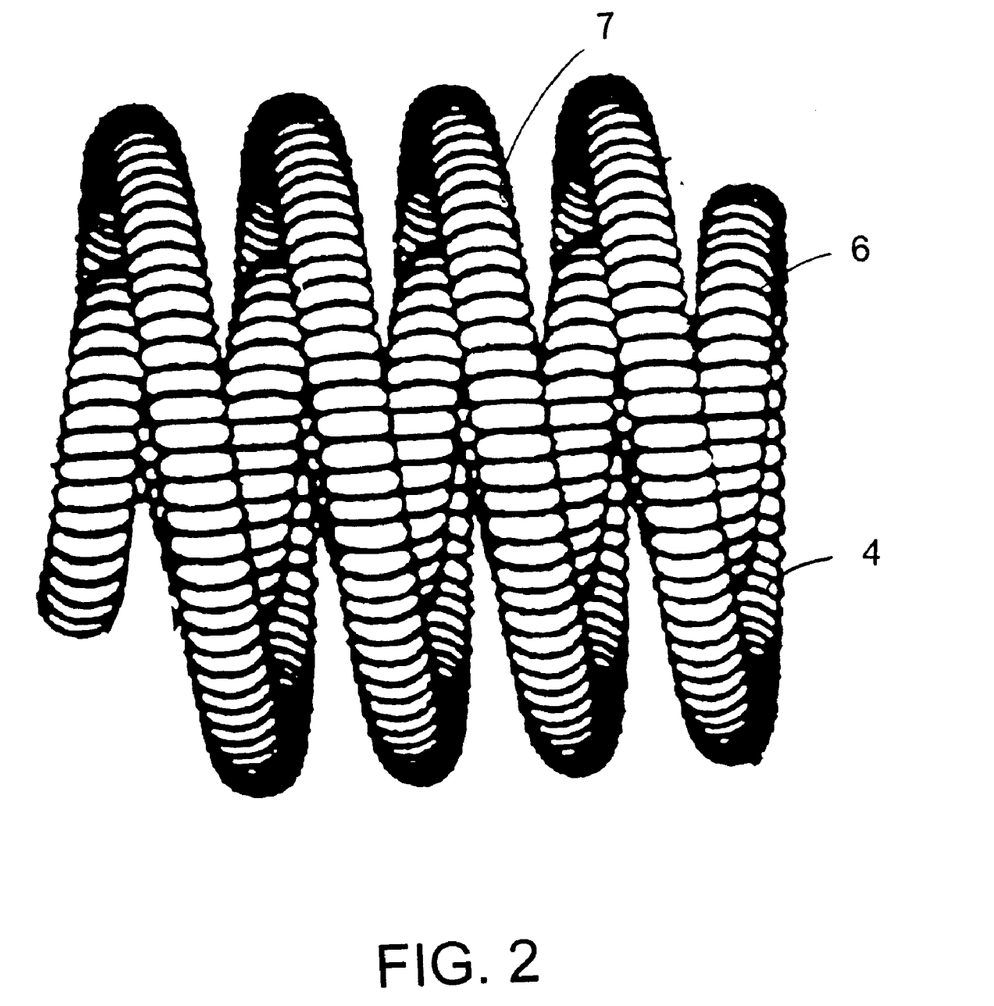
FIG. 2 shows an occlusion element.
Figure 3:
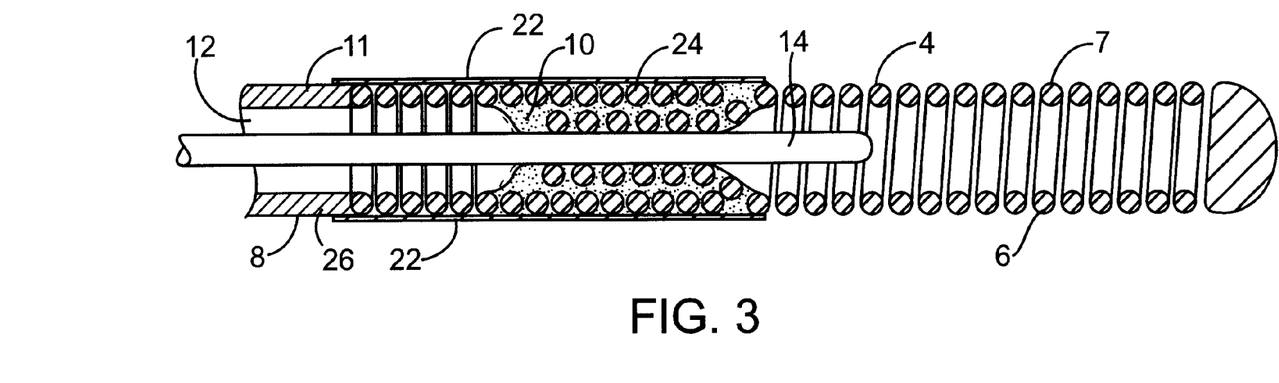
FIG. 3 shows the occlusion element mounted to a delivery element.
Figure 4:
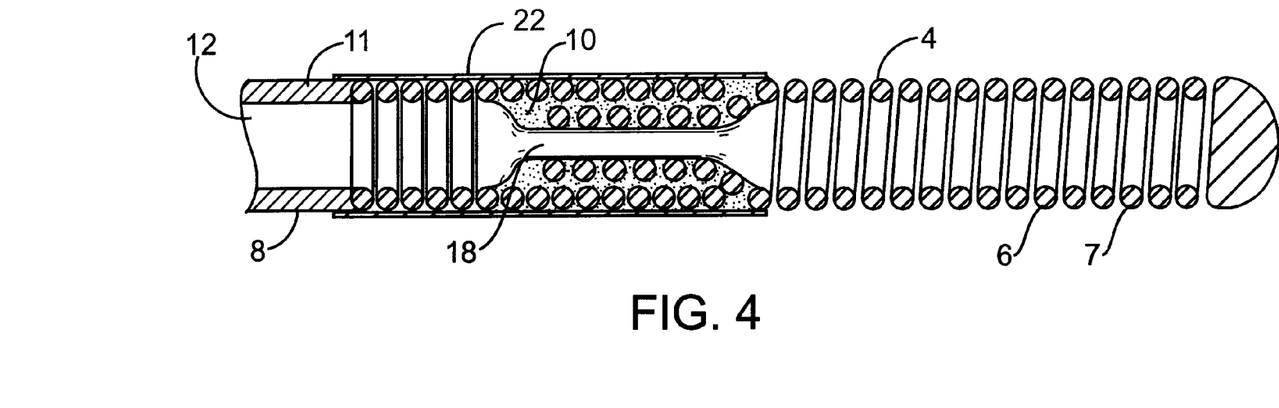
FIG. 4 shows the distal end of the delivery element with a blocking element removed from a cavity in the dissolvable material.
Figure 5:
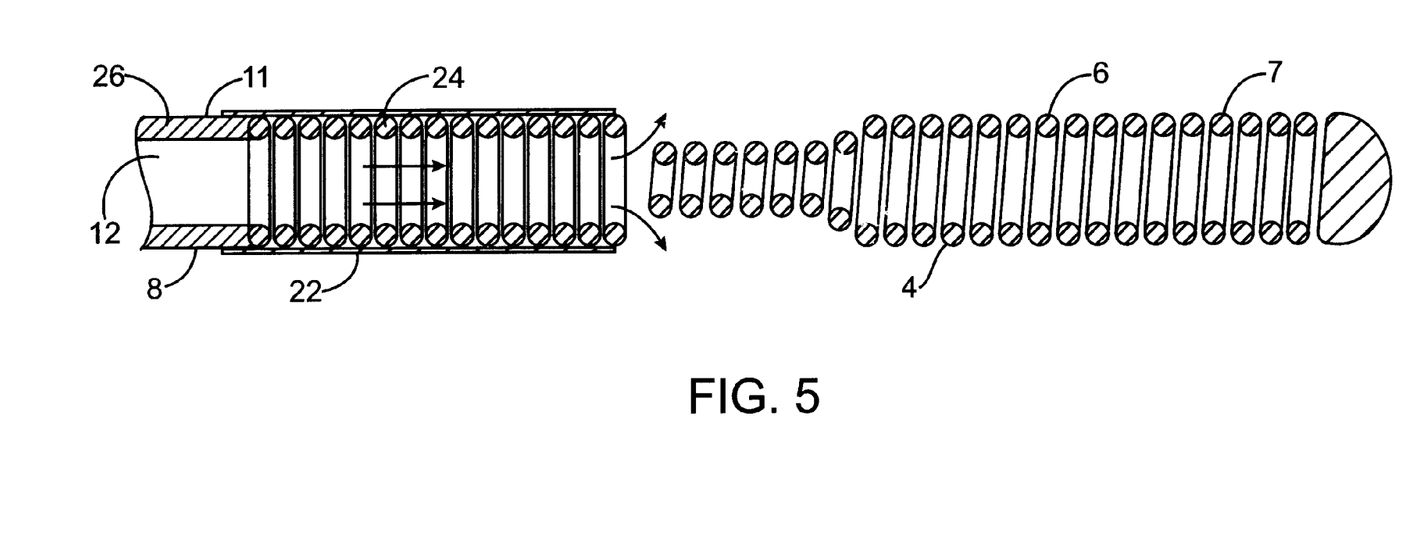
FIG. 5 shows the distal end of the delivery element with the dissolvable material dissolved and the occlusion element released.

The system 2 of FIG. 1 shows delivery of the occlusion element 6 to the cerebral vasculature, however, the system, devices and methods of the present invention may be used to deliver the occlusion element 6 to any location in the patient. The system 2 includes a guide catheter 5 which is advanced to a suitable location. A microcatheter or sheath 12 may then be advanced through the guide catheter 5. The delivery element 8 is then advanced through the microcatheter to the desired release site. The microcatheter or sheath 12 may hold the occlusion element 6 in a collapsed condition as demonstrated in the patents incorporated by reference above. The element 6 forms the coiled structure of FIG. 2 as it exits the distal end of the sheath 12. The delivery element 8 may receive a blocking element 14 which is described in further detail below. A fluid circulating device 15, such as a source of fluid 16, is coupled to the delivery element 8 for delivery of a fluid to dissolve the material 10 as also described in greater detail below. The fluid may be any suitable fluid and is preferably saline but may also be the patient's own blood, a mixture of saline and contrast to visualize the area or any combination thereof.

The occlusion element 6 is mounted to the delivery element 8 with the fluid dissolvable material 10 which forms a dissolvable bond 12. The fluid is preferably delivered to the dissolvable material 10 from the source of fluid 16 so that the dissolution of the material 10 may be controlled by delivery of the fluid. Although it is preferred to circulate the fluid to dissolve the material 10, the fluid may also simply be the patient's own blood. Such a device may be practiced with various aspects of the invention described herein without departing from the scope of the invention.

The blocking element 14 may be used to protect parts of the dissolvable material 10 during introduction and advancement of the occlusion element 6. The blocking element 14 may simply be a wire, guidewire, mandrel or even a tube. The blocking element 14 may be positioned adjacent or against any portion of the material 10 and is preferably positioned in a cavity 18 in the material 10. The cavity 18 is shown as a throughhole 20 but may take any other shape such as a hole closed on one end. The blocking element 14 temporarily blocks the cavity 18 to inhibit dissolution of the material 10. When the blocking element 14 is withdrawn, part of the material 10 is exposed thereby permitting dissolution of the material 10. Of course, fluid may be in contact with the material 10 even with the blocking element 14 positioned in the cavity, however, the blocking element 14 will at least inhibit fluid flow around the dissolvable material 10 thereby preventing premature dissolution of a substantial portion of the material 10.

The delivery element 8 may include a sheath 22 extending over an outer surface of the dissolvable material 10. The sheath 22 protects the outer surface of the material 10 to inhibit dissolution of the material 10. The sheath 22 may be any suitable flexible sheath and may be made of any suitable material such as PET. The delivery element 8 has a coil 24 coupled to a tube 26. The coil 24 provides a flexible distal end for advancement of the delivery element 8 through tortuous vessels. The sheath 22 may extend over the coil 24 and tube 26 or only over a portion of the coil 24 and material 10.

Figure 6:
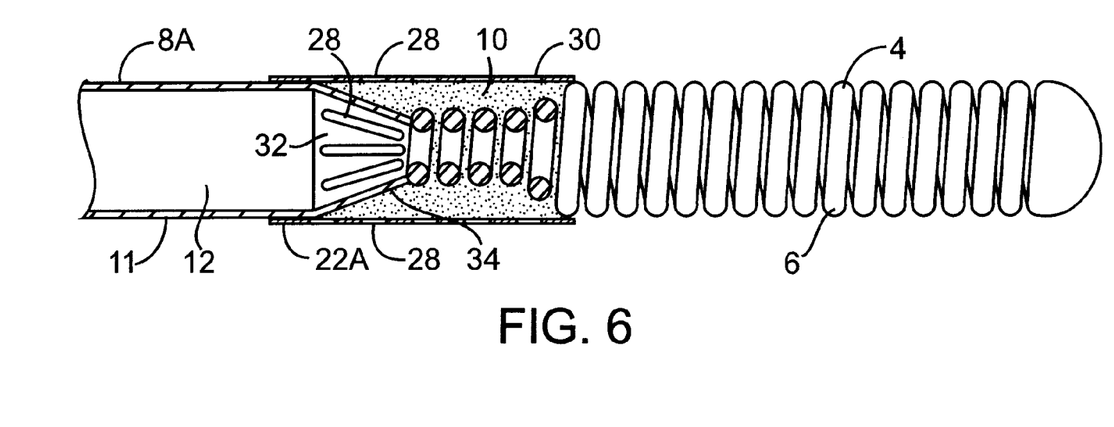
FIG. 6 shows another device for delivering the occlusion element.
Figure 7:
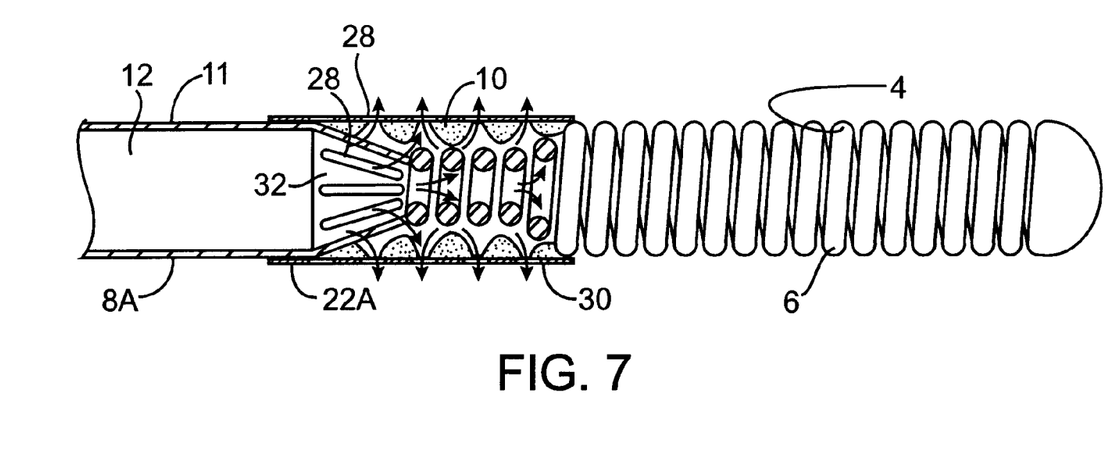
FIG. 7 shows the device of FIG. 6 after partial dissolution of the material.
Figure 8:
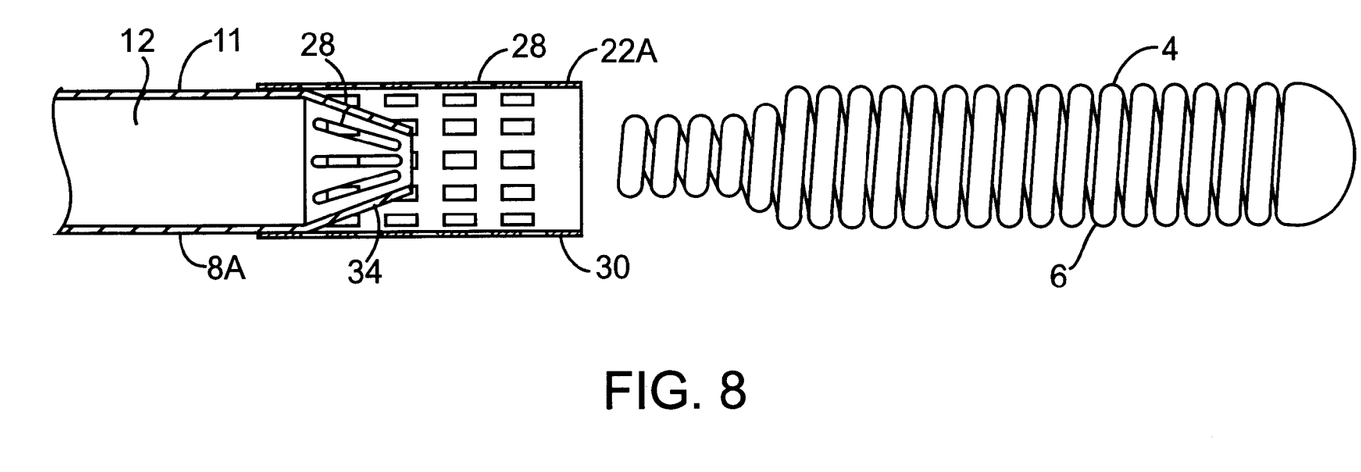
FIG. 8 shows the occlusion element released from the delivery device.

Referring to FIGS. 6–8, an alternative device for delivering the occlusion element 6 is shown wherein the same or similar reference numbers refer to the same or similar structure. The delivery element 8A has openings 28 therein through which fluid is delivered when dissolving the material 10. The openings 28 may be in the sheath 22A extending over the material 10. The openings 28 may also be one or more slits 30 in the sheath 22A which open when positive pressure is applied so that the slit 30 acts as a valve which opens when the fluid is delivered yet covers the material 10 during introduction and advancement. The openings 28 may also be part of a portion 32 of the delivery element 8 which extends into the material 10. The portion 32 extending into the material 10 may, for example, be a conical section 34. The openings 28 serve as fluid channels when dissolving the material 10 so that the material 10 may be dissolved relatively quickly at the desired time. An advantage of such a design is that the dissolvable material 10 may be kept relatively robust while maintaining the ability to quickly dissolve the bond at the appropriate time. Use of the blocking element 14 (FIG. 2) further enhances the ability to control dissolution of the dissolvable material 10 as discussed above and specifically incorporated here.

Figure 9:
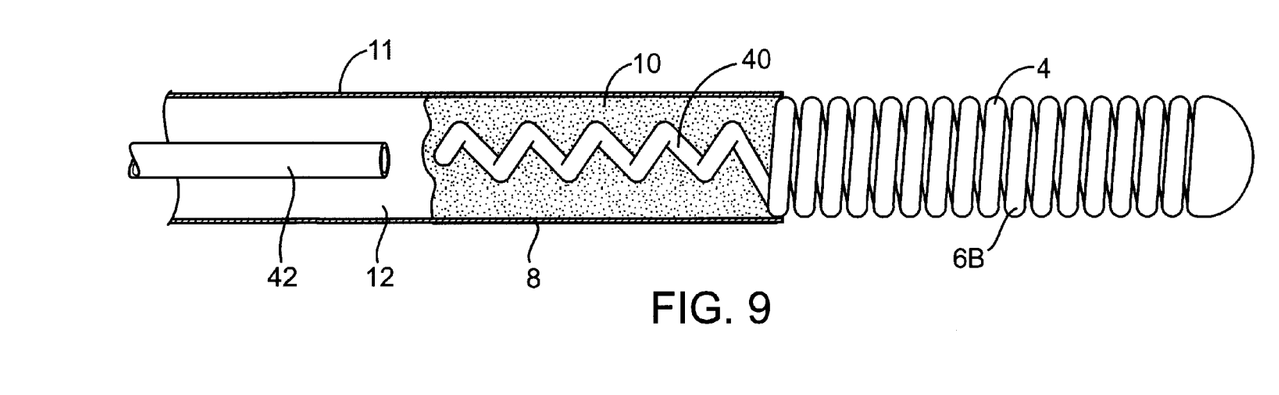
FIG. 9 shows still another device for delivering an occlusion element.
Figure 10:
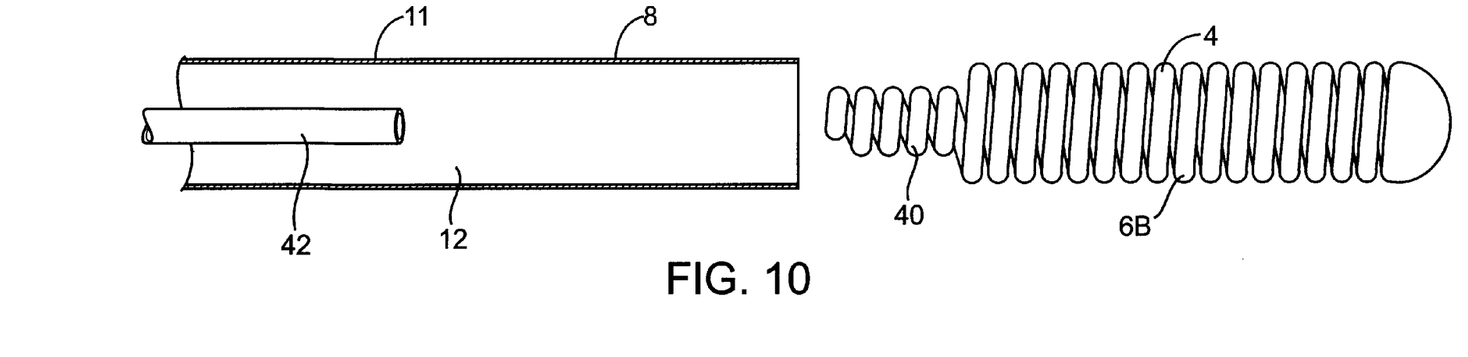
FIG. 10 shows the occlusion element of FIG. 10 released from the delivery element.

Referring to FIGS. 9 and 10, still another device for delivering an occlusion element 6B is shown wherein the same or similar reference numbers refer to the same or similar structure. The occlusion element 6B has a portion 40 embedded in the dissolvable material 10. The portion 40 is preferably naturally biased toward the collapsed position of FIG. 10 when released. The dissolvable material 10 is shown as a solid plug of material 10 but may, of course, have the cavity or throughhole as shown in connection with FIGS. 3–8 without departing from the scope of the invention. A tube 42 is used to deliver, withdraw or otherwise circulate the fluid to dissolve the material 10 at the desired time. The tube 42 and lumen 12 in the delivery element 8 are coupled to the fluid circulating devices 15. The fluid circulating devices 15 may be either the fluid source 16 with pump or a fluid withdrawal device 17, such as a vacuum source or vacuum pump, which are used to circulate the fluid around the material 10. For example, the fluid may be delivered through either the tube 42 or through the annular area between the delivery element 8 and tube 42 with the other element being used to withdraw the fluid. Alternatively, the tube 42 may be used with the fluid withdrawal device 17 to withdraw fluid into the tube 42 while drawings the fluid through the lumen 12. Of course, the fluid may also be simply pulsed one way and then the other so long as the fluid is generally being circulated through the area to dissolve the material 10. One advantage of such as system is that the dissolved material 10 may be withdrawn through the delivery element 8 or tube 42.

The tube 42 and annular area between the delivery element 8 and tube 42 may also be used to prime the device with a suitable fluid. The priming fluid may a fluid which does not dissolve the material 10 or which dissolves the material 10 very slowly. The tube 42 and annular area between the delivery element 8 and tube 42 may also be used to actively remove air as well as for delivery of the fluid after advancing the device to the desired release site. Although the devices described herein include a separate tube 42, the device 8 may also simply have two lumens instead of the tube 42 without departing from the scope of the invention.

Figure 11:
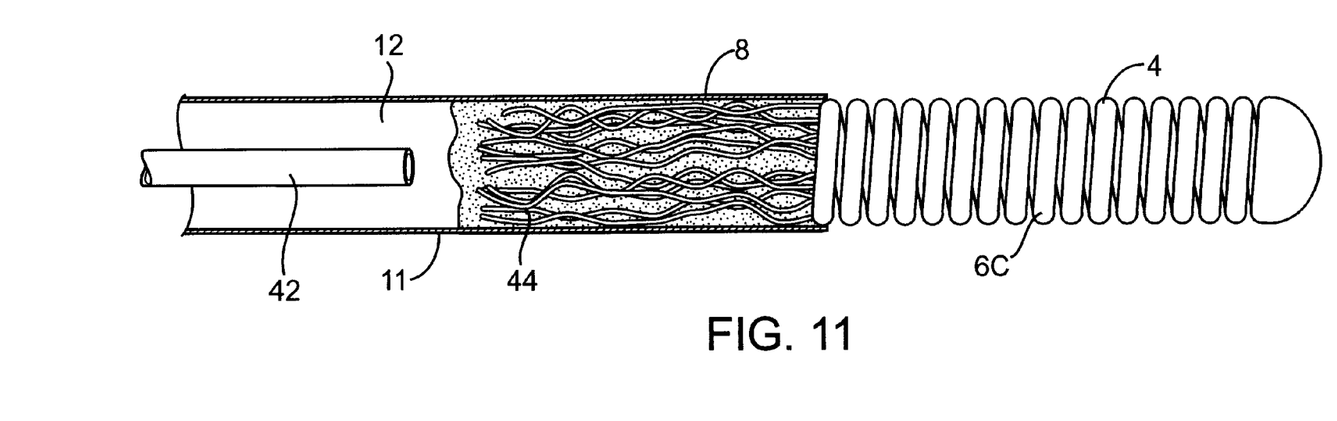
FIG. 11 shows yet another device for delivering an occlusion element.
Figure 12:
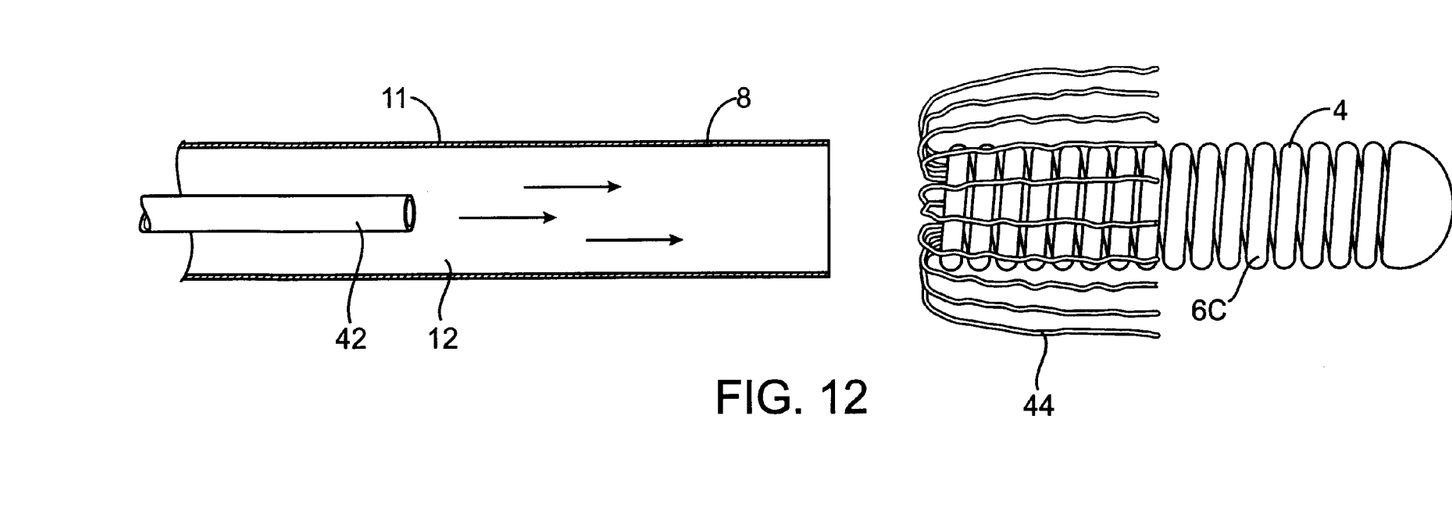
FIG. 12 shows the occlusion element of FIG. 11 released from the delivery element.
Figure 13:
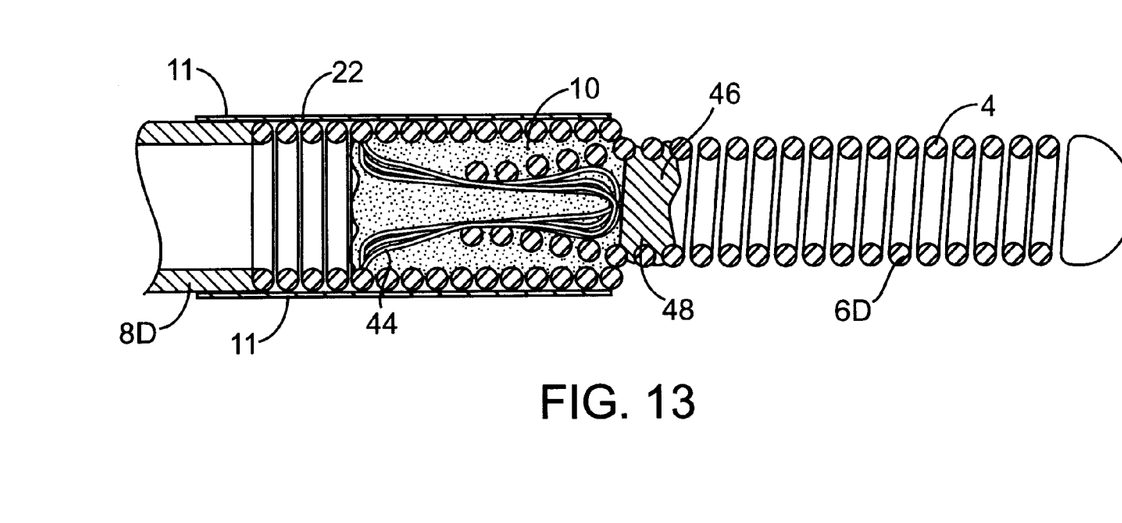
FIG. 13 shows yet another device for delivering an occlusion element.
Figure 14:
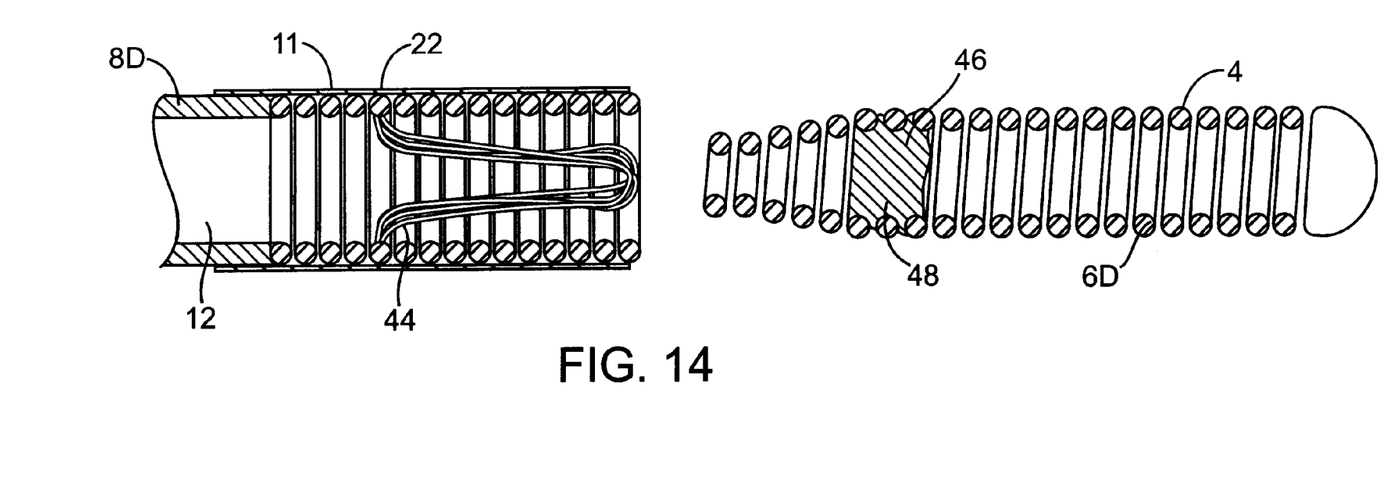
FIG. 14 shows the occlusion element of FIG. 13 released from the delivery element.

Referring to FIGS. 11 and 12, yet another device for delivering an occlusion element 6C is shown wherein the same or similar reference numbers refer to the same or similar structure. The occlusion element 6C has a plurality of filaments 44 embedded in the dissolvable material 10. The tube 42 may be used to circulate the fluid and dissolve the material 10 at the desired time. Referring to FIGS. 13 and 14, still another device 8D for delivering an occlusion element 6D is shown wherein the same or similar reference numbers refer to the same or similar structure. The delivery element 8D has a plurality of filaments 44 embedded in the dissolvable material 10. An advantage of the device 8D is that the filaments 44 are not part of the occlusion element 6D so that the occlusion element 6C may be substantially a conventional occlusion element 6D. The occlusion element 6D also has a distal block 46, which inhibits, and preferably prevents, fluid from entering the distal end of the delivery element 8 to protect the dissolvable material 10 from exposure to blood. The distal block 46 is preferably solder 48 but may be any other suitable material 10.

Figure 15:
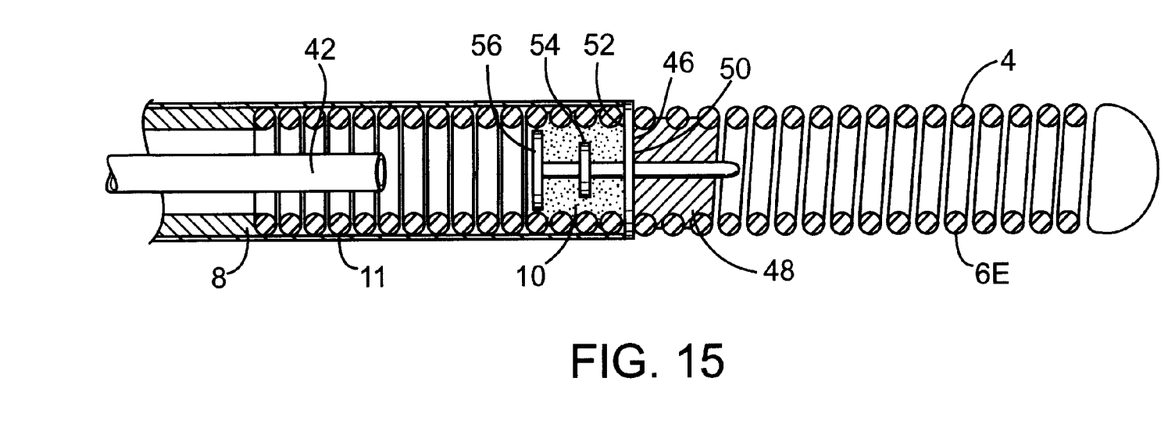
FIG. 15 shows another device for delivering an occlusion element with the occlusion element inhibiting fluid contact with the material.
Figure 16:
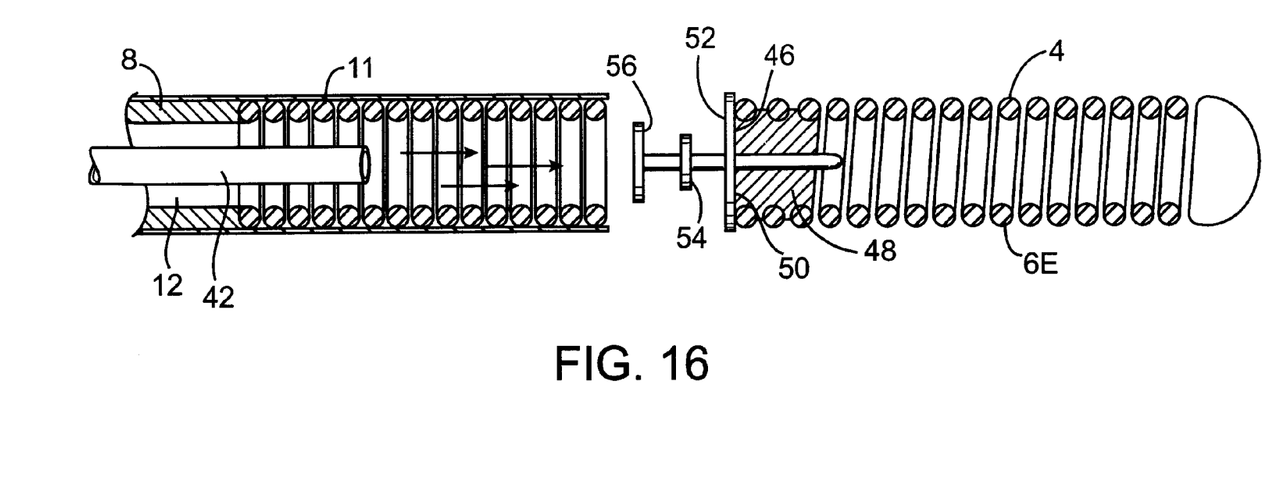
FIG. 16 shows the occlusion element of FIG. 16 released from the delivery element.

Referring to FIGS. 15 and 16, yet another device for delivering an occlusion element 6E is shown. The occlusion element 6E has a blocking element 50, which is preferably a first disc 52, which prevents exposure of the material 10 to blood. A second disc 54, or other suitable shape, anchors the occlusion element 6 to the material 10. A third disc 56 serves to move the coil out of the delivery element 8 after melting of the dissolvable material 10. The pressure of the fluid is increased so that the pressure forces on the third disc 56 push the occlusion element 6E out of the delivery element 8. The third disc 56, of course, does not completely prevent proximal exposure of the dissolvable material 10 since the fluid is delivered through the delivery element 8, preferably with the tube, to melt the dissolvable material 10.

Figure 17:
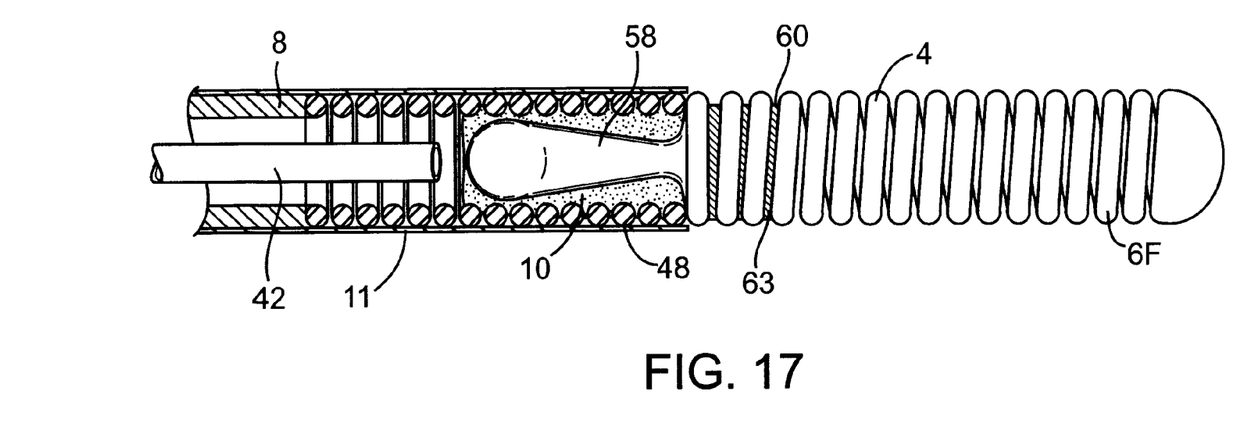
FIG. 17 shows still another device for delivering an occluding element.
Figure 18:
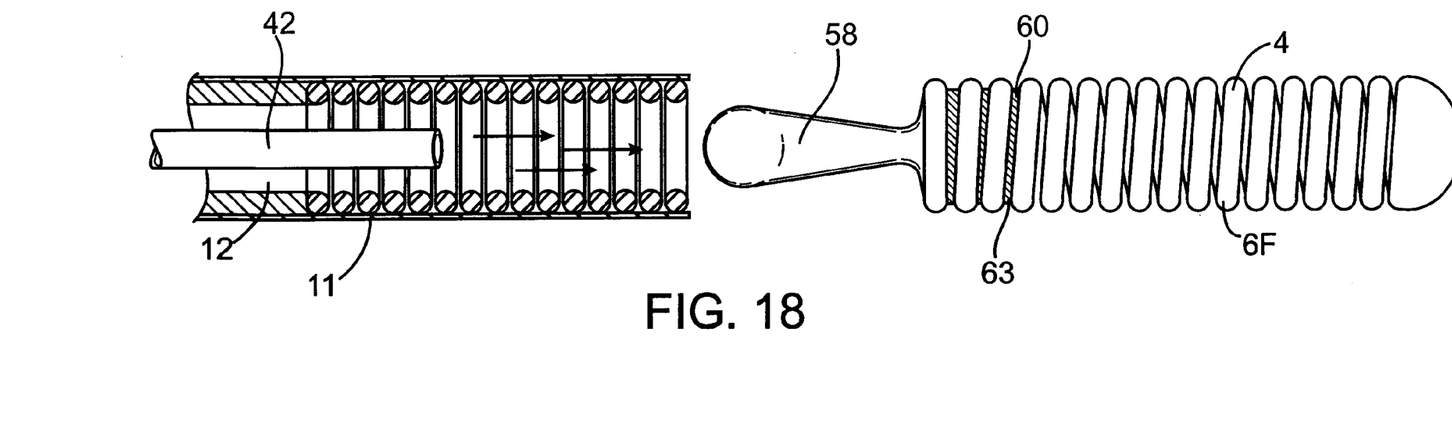
FIG. 18 shows the occlusion element of FIG. 17 released from the delivery element.
Figure 19:
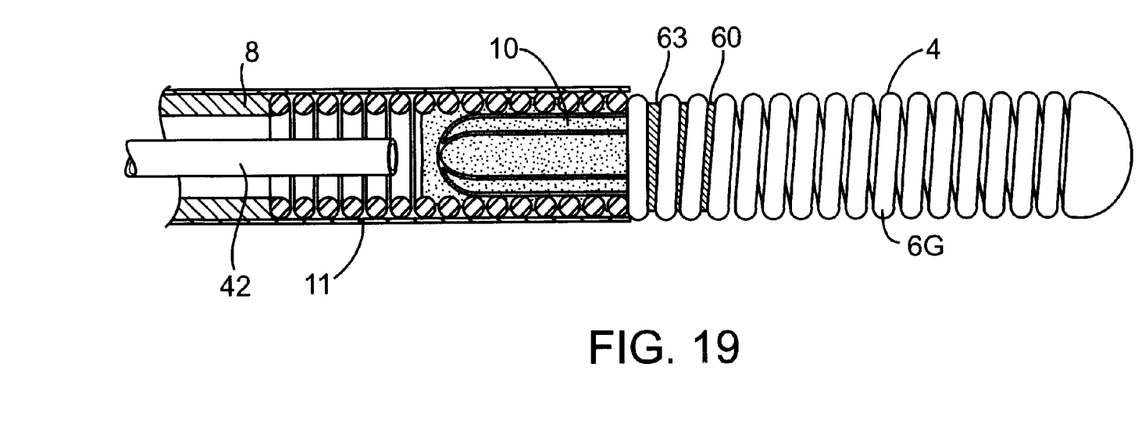
FIG. 19 shows still another device for delivering an occluding element.
Figure 20:
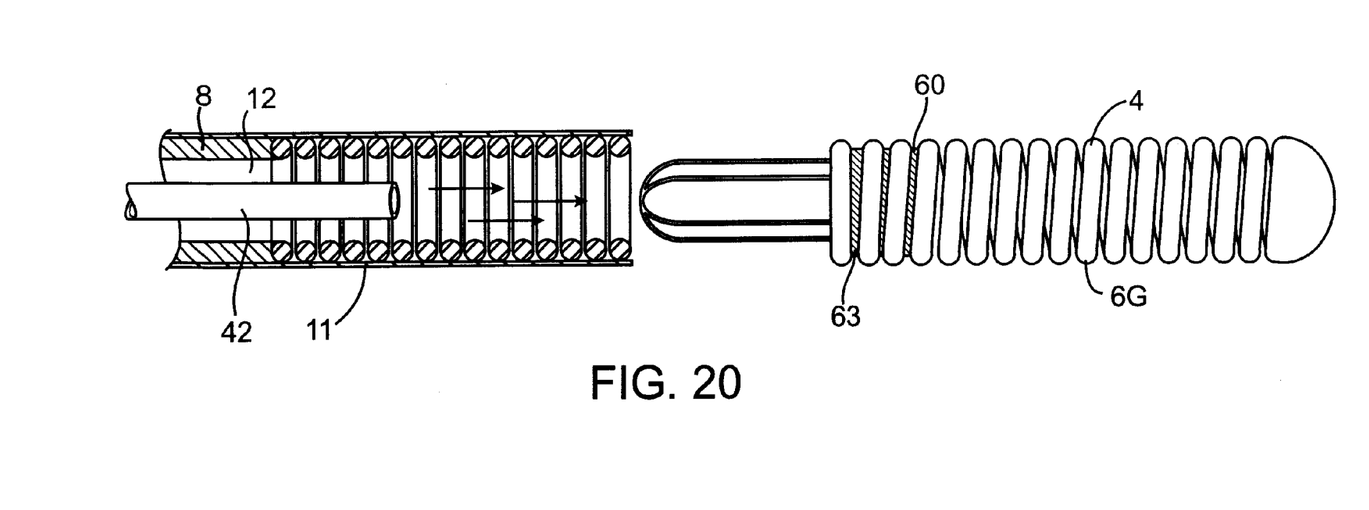
FIG. 20 shows the occlusion element of FIG. 19 released from the delivery element.

Referring to FIGS. 17 and 18, another occlusion element 6F is shown. The occlusion element 6F has a ball 58, preferably 1–2 mm in diameter, embedded in the material 10. The ball 58 is attached to the rest of the occlusion element 6F with solder 60 which also serves as a blocking element 63 to prevent distal exposure of the dissolvable material 10. Referring to FIGS. 19 and 20 still another occlusion element 6G is shown which has a cage 62 embedded in the material 10. The cage 62 is attached to the rest of the occlusion element 6 with solder 60 which also serves as the blocking element 63 to prevent distal exposure of the dissolvable material 10.

A method of delivering a medical device, such as an occlusion element 6, is now described in connection with the preferred embodiments, however, it is understood that the method may be practiced with any suitable device. As mentioned above, the invention may be used in any location in the patient's body and use in the cerebral vasculature is described as a particular use of the invention although any other medical device may be delivered to any other part of the body for any other purpose. The guide catheter 5 is introduced into a vessel, such as the femoral artery, and advanced to a suitable location. The microcatheter 12 is then advanced through the guide catheter 5 to a location near the desired site for releasing the occlusion element 6. The invention may be practiced with fewer or more delivery catheters, cannulae or sheaths without departing from the scope of the invention.

The occlusion element 6 is delivered to the desired location by manipulating the delivery element 8. At the desired release time and location, the blocking element (FIG. 2), if used, may be moved to expose at least part of the dissolvable material 10. Fluid is then delivered with the delivery element 8 and/or tube 42 to dissolve the material 10 and release the occlusion element 6. Depending upon the particular embodiment, the release of the occlusion element from the dissolvable bond may completely release the occlusion element 6 from the delivery element 8 or the delivery element 8 may need to be withdrawn to completely release the occlusion element 6. An advantage of requiring additional withdrawal of the delivery element is that the occlusion element 8 may still be manipulated to some degree after release from the dissolvable bond. For example, the delivery element 8 may be advanced and manipulated further to move the occlusion element 8 after dissolution of the material 10.

The present invention has been described in connection with the preferred embodiments, however, many variations and alternative embodiments fall within the scope of the invention. For example, the occlusion element may have any shape and may be made of any material. Furthermore, although it is preferred to deliver the fluid to the dissolvable material, the material may also be dissolved by simply coming into contact with the patient's blood without departing from various aspects of the invention. The dissolvable material may completely detach the occlusion element from the delivery element or may require another action, such as withdrawal of the delivery element, to fully release the occlusion element. Finally, the methods and devices of the present invention may be used with any medical device and not necessarily the occlusion elements described herein. Thus, the description of the preferred embodiments should not limit the invention. The invention has been described in connection with a number of different features, aspects and advantages which should be considered independently and, thus, no single aspect or advantage of the invention should be considered an essential element of the invention. For example, various aspects of the invention may be practiced with or without various aspects such as the blocking element, sheath, or fluid circulation.

What is claimed is:

1. A method of delivering an occlusion element, comprising the steps of:

providing an occlusion element which is coupled to a delivery element with a dissolvable material, the dissolvable material being dissolvable with a fluid, the dissolvable material forming a dissolvable connection between the delivery element and the occlusion element;

advancing the occlusion element through a patient's vascular system with the occlusion element coupled to the delivery element with at least the dissolvable connection; and dissolving the dissolvable material thereby releasing the occlusion element from the dissolvable connection with the delivery element.

2. The method of claim 1, wherein:

the dissolving step is carried out by delivering the fluid to the material to dissolve the dissolvable material.

3. The method of claim 2, wherein:

the dissolving step is carried out with the fluid being delivered through the delivery element.

4. The method of claim 3, wherein:

the dissolving step is carried out with a tube positioned in the delivery element, the tube having a lumen, the tube and delivery element defining a space therebetween, the fluid being delivered through one of the lumen and the space and the fluid being withdrawn through the other of the lumen and the space.

5. The method of claim 1, wherein:

the providing step is carried out with the occlusion element forming coils.

6. The method of claim 1, wherein:

the providing step is carried out with the dissolvable material having a cavity.

7. The method of claim 6, wherein:

the providing step is carried out with the cavity being a throughhole.

8. The method of claim 1, further comprising the step of:

positioning a blocking element to impede fluid contact with a least a protected portion of the dissolvable material, the blocking element being movable to a position spaced apart from the protected portion of the dissolvable material.

9. The method of claim 8, wherein:

the blocking element is positioned in a cavity in the dissolvable material.

10. The method of claim 1, wherein:

the providing step is carried out with the occlusion element having a portion embedded in the dissolvable material.

11. The method of claim 10, wherein:

the providing step is carried out with the embedded portion being embedded in the dissolvable material in an expanded position, the embedded portion being naturally biased toward a collapsed position; and the dissolving step is carried out so that the portion of the occlusion element is no longer embedded in the material thereby permitting the portion to move toward the collapsed position.

12. The method of claim 10, wherein:

the providing step is carried out with the portion embedded in the material including a plurality of filaments.

13. The method of claim 10, wherein:

the providing step is carried out with the portion embedded in the dissolvable material being a coil.

14. The method of claim 1, wherein:

the providing step is carried out with the occlusion element having a plurality of flexible fibers embedded in the dissolvable material.

15. The method of claim 1, wherein:

the providing step is carried out with the portion embedded in the material including a ball.

16. The method of claim 1, wherein:

the providing step is carried out with the portion embedded in the material including a cage.

17. The method of claim 1, wherein:

the providing step is carried out with a flexible sheath covering at least a portion of the dissolvable material.

18. The method of claim 17, wherein:

the providing step is carried out with the sheath having openings therein.

19. The method of claim 18, wherein:

the providing step is carried out with the delivery element having a fluid distributing portion with openings for distributing the fluid;

the dissolving step being carried out to deliver the fluid through the openings in the distributing portion to dissolve the material.

20. The method of claim 19, wherein:

the providing step is carried out with the distributing portion being conical.

21. The method of claim 1, further comprising the step of:

moving the delivery element relative to the occlusion element after the dissolving step to fully release the occlusion element from the delivery element.

22. The method of claim 1, wherein:

the dissolving step fully releases the occlusion element from the delivery element.

23. The method of claim 1, wherein:

the providing step is carried out with the occlusion element having a blocking portion which isolates the material from the patient's blood;

the advancing step being carried out so that the blocking portion isolates the material from the patient's blood during the advancing step.

24. The method of claim 23, wherein:

the providing step is carried out with the blocking portion being a plug of material.

25. The method of claim 24, wherein:

the providing step is carried out with the plug of material being solder.

26. The method of claim 23, wherein:

the providing step is carried out with the blocking portion being a disc.

27. The method of claim 1, wherein:

the dissolving step is carried out with the fluid being a fluid selected from the group consisting of water, saline and the patient's own blood.

28. The method of claim 1, wherein:

the providing step is carried out with the material being selected from the group consisting of sugar, salt, manitol or a combination thereof.

* * * * *